(12) United States Patent
Gauthier et al.

(10) Patent No.: US 10,279,377 B2
(45) Date of Patent: May 7, 2019

(54) METHOD FOR SORTING CONTAMINATED CATALYSTS OR ADSORBENTS

(71) Applicants: EURECAT S.A., La Voulte sur Rhone (FR); IFP Energies nouvelles, Rueil-Malmaison (FR)

(72) Inventors: Thierry Gauthier, Brignais (FR); Charles-Philippe Lienemann, Villemoirieu (FR); Wilfried Weiss, Valencin (FR); Pierre Dufresne, Aouste sur Sye (FR); Pauline Galliou, Sant Laurent du Pape (FR)

(73) Assignees: EURECAT S.A., La Voulte sur Rhone (FR); IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 15/579,854

(22) PCT Filed: Jun. 3, 2016

(86) PCT No.: PCT/EP2016/062724
§ 371 (c)(1),
(2) Date: Dec. 5, 2017

(87) PCT Pub. No.: WO2016/193478
PCT Pub. Date: Dec. 8, 2016

(65) Prior Publication Data
US 2018/0154397 A1    Jun. 7, 2018

(30) Foreign Application Priority Data

Jun. 5, 2015  (FR) ..................................... 15 55167

(51) Int. Cl.
*B07C 5/346* (2006.01)
*B01J 38/72* (2006.01)
(Continued)

(52) U.S. Cl.
CPC ............... *B07C 5/346* (2013.01); *B01J 21/04* (2013.01); *B01J 23/882* (2013.01); *B01J 23/883* (2013.01);
(Continued)

(58) Field of Classification Search
CPC ..... B07C 5/342; B07C 5/3425; B07C 5/3427; B07C 5/344; B07C 5/346; B01J 23/94; B01J 38/72; G01N 21/718
(Continued)

(56) References Cited

U.S. PATENT DOCUMENTS 4,723,660 A * 2/1988 Sjoberg ................. B07B 13/065
209/622
5,396,071 A * 3/1995 Atwell ................. G01N 23/222
198/811
(Continued)

FOREIGN PATENT DOCUMENTS

EP        2008726 A1   12/2008
WO   2012168938 A1   12/2012
(Continued)

OTHER PUBLICATIONS

International Search Report PCT/EP2016/062724 dated Aug. 8, 2016.
(Continued)

*Primary Examiner* — Joseph C Rodriguez
(74) *Attorney, Agent, or Firm* — Millen, White, Zelano and Branigan, P.C.

(57) ABSTRACT

A method and a device for separation of at least one catalyst and/or adsorbent from a homogeneous mixture of catalysts and/or adsorbents containing one or more metal, semi-metal or non-metal contaminant(s) deposited thereon, making it possible to separate catalysts or adsorbents according to the presence or absence of contaminant and also according to
(Continued)

the contaminant content, starting from a sorting threshold that corresponds to a content and that is defined by the operator.

16 Claims, 2 Drawing Sheets

(51) Int. Cl.
*B07C 5/00* (2006.01)
*B07C 5/36* (2006.01)
*G01N 21/71* (2006.01)
*B01J 23/94* (2006.01)
*B01J 35/00* (2006.01)
*B01J 21/04* (2006.01)
*B01J 23/882* (2006.01)
*B01J 23/883* (2006.01)
*B01J 23/888* (2006.01)
*B01J 37/00* (2006.01)
*B01J 23/90* (2006.01)

(52) U.S. Cl.
CPC ............ *B01J 23/888* (2013.01); *B01J 23/94* (2013.01); *B01J 35/0006* (2013.01); *B01J 37/009* (2013.01); *B01J 38/72* (2013.01); *B07C 5/00* (2013.01); *B07C 5/368* (2013.01); *G01N 21/718* (2013.01); *B01J 23/90* (2013.01); *B07C 5/366* (2013.01)

(58) Field of Classification Search
USPC .................................................. 209/576, 579
See application file for complete search history.

(56) References Cited

U.S. PATENT DOCUMENTS

| | | | |
|---|---|---|---|
| RE35,046 E * | 10/1995 | Hettinger, Jr. | ............. B01J 8/42 208/113 |
| 6,545,240 B2 * | 4/2003 | Kumar | ................. B07C 5/3425 209/579 |
| 7,200,200 B2 * | 4/2007 | Laurila | ................ G01N 23/223 250/269.3 |
| 7,253,414 B2 * | 8/2007 | Osucha | .................. G01N 23/12 250/358.1 |
| 7,803,627 B2 * | 9/2010 | Hodges | .................. C10G 9/005 208/131 |
| 7,886,915 B2 | 2/2011 | Shulman | |
| 8,307,985 B2 | 11/2012 | Dufresne | |
| 8,861,675 B2 * | 10/2014 | Sommer, Jr. | ........... G01N 23/06 378/53 |
| 9,476,829 B2 | 10/2016 | Nagli | |
| 9,855,588 B2 | 1/2018 | Gauthier | |
| 2009/0000992 A1 | 1/2009 | Dufresne | |
| 2013/0073077 A1 | 3/2013 | Wellwood | |
| 2013/0264249 A1 | 10/2013 | Sommer, Jr. | |
| 2014/0260801 A1 | 9/2014 | Wellwood | |

FOREIGN PATENT DOCUMENTS

WO 2015082424 A1 6/2015
WO 2013013276 A1 12/2016

OTHER PUBLICATIONS

Yasmina Tayeb: "Le projet Trisur, lauréat du concours mondial d'innovation", La Tribune, Sep. 2, 2014 (Sep. 2, 2014), XP055262244, Retrieved from the Internet [retrieved on Apr. 1, 2016].
Asimellis G et al: "Platinum group metals bulk analysis in automobile catalyst recycling material by laser-induced breakdown spectroscopy", Spectrochimica Acta. Part B: Atomic Spectroscopy, New York, NY, US, US, vol. 63, No. 11, Nov. 1, 2008 (Nov. 1, 2008), pp. 1338-1343, XP025685358, ISSN: 0584-8547, [retrieved on Oct. 9, 2008].

* cited by examiner

METHOD FOR SORTING CONTAMINATED CATALYSTS OR ADSORBENTS

The invention relates to a method and a device for separation (sorting) of contaminated catalyst or adsorbent.

More specifically, the invention relates to a method and a device for separation (sorting) of at least one catalyst and/or at least one adsorbent from a homogeneous mixture of catalysts and/or adsorbents, with the catalysts or adsorbents containing, after use, non-metal contaminants such as carbon, sulfur, nitrogen, chlorine, silicon, phosphorus or sodium, or metal contaminants such as nickel, vanadium, iron, mercury, or semi-metal contaminants such as arsenic.

These contaminants are generally contained in the feedstocks that are treated by these catalysts or these adsorbents, or can be obtained from secondary reactions such as coking. The method and the device for separation and sorting make it possible to separate the catalysts and/or the adsorbents that are obtained from a mixture of catalysts or adsorbents based on the content of contaminants that are present in the catalysts or the adsorbents, with the sorting threshold being defined by the operator.

STATE OF THE ART

In the U.S. Pat. No. 7,886,915, a method is described for in-line sorting of metal scraps (scrap iron, ferrous and non-ferrous shavings). The proposed system is an in-line analysis system that makes it possible to determine the chemical composition of the elements to be sorted. In this invention, the materials to be sorted are metal parts whose shape and size are variable and not determined. One of the objects of the invention relates to implementing the analysis in bulk, rather than analyzing each particle individually. The targeted industrial application relates to the recycling of scrap iron; with the former then being melted in electric furnaces, it is important for the quality of the final steel to eliminate as well as possible the non-ferrous metals and particularly copper.

The patent application US 2013/0073077 A1 relates to a sorting system adapted to ores. The proposed analysis means associated with sorting are many and preferably relate to the Near Infrared (NIR) technique or the LIBS (Laser Induced Breakdown Spectroscopy) technique, X rays or magnetic detectors.

There again, these are particles of undefined size, with the ore to be sorted resulting from an initial grinding or crushing process. An ore contains metal elements that are mixed with rock whose crystalline shapes and chemical composition can vary. The concentration in metals is variable from one particle to the next. In this type of application, an attempt is made in general to sort the particles so as to keep those whose desired metal element composition is the largest.

The patent application WO2013/013276 A1 also describes a sorting system adapted to ores in a context that is similar to the patent application US 2013/0073077 A1. The shape and the size of the elements to be sorted is variable, their composition also since these are ores. An arrangement of the particles on the conveyor belt is claimed to make possible the sorting capacity of the particles. It is proposed in particular to monitor the spacing between the different particles on the conveyor belt of the sorting chain. In a preferred manner, a system for arrangement in rows transverse to the direction of flow on the belt is proposed.

Finally, in the application WO2012/168938 A1, a sorting system is proposed, there again preferably applied to the sorting of ore, with a strong quantitative feature making it possible to set a rejection threshold on the basis of a minimum content of one of the desired elements. The in-line detection means are based on two lasers, and a double-pulse system makes it possible to take an absorption reading that differs from the emission reading that is conventionally used in the LIBS technique.

The patent application US 2013/264249 describes a method for the sorting of objects that contain recyclable materials by X fluorescence. The size of the analyzed zone is on the order of several cm.

All of these techniques have been developed within the framework of mining with rough sorting. The sorting on catalysts requires a more precise approach to ensure the maximum recovery of metals, given the high cost of catalysts and the potential added value.

The patent EP-2008726 proposes a sorting of spent catalysts according to the color of their surface, more or less gray.

This invention makes it possible to increase the reuse of catalysts or adsorbents in the methods and thus to limit the quantities intended for the final recycling, the final recycling being a destructive method making it possible to recover at least in part the upgradable components that are contained in the catalysts or adsorbents.

The catalysts and adsorbents that are used in the industry, in particular the chemical industry, the industries for the production and refining of hydrocarbons (gas, petroleum), the methods for treatment of biomass and/or carbon, are often exposed to the presence of numerous contaminants that are present in the feedstocks that are to be treated and that are deposited on the catalyst or on the adsorbent in the reactors or adsorbers. These contaminants have different natures. After interaction between the feedstock and the catalyst or the adsorbent, these contaminants will be deposited on the solid, which leads to a gradual deterioration of the catalytic properties of the catalyst or the properties for separation of the adsorbent.

It will be noted that the contaminants are different from the constituent elements of the catalyst or the adsorbent, even if in some cases, this is the same chemical element. Actually, the constituent elements are an integral part of the catalyst or the adsorbent. They are brought in during the manufacturing and take part in the catalytic activity of the catalyst or in the selectivity of the adsorbent.

Among the frequently-encountered non-metal contaminants, there are, for example, C, S, N, Cl, P and Na. Among the frequently-encountered metal contaminants, there are, for example, Ni, V, Fe, Hg, and among the semi-metal contaminants, there is most often As.

The contents of contaminants deposited on the catalyst or on the adsorbent are variable. They can vary in the same catalytic bed depending on the height in the reactor or the radial position. These important gradients are in general observed, more or less marked, depending on the decomposition kinetics of the molecules that contain these elements.

During unloading, there is then a mixture of catalysts or adsorbents having different contaminant contents.

Treatments make it possible to eliminate certain contaminants such as carbon and sulfur without thereby eliminating other contaminants, such as, for example, Ni, V, Fe, As, Na, P.

Thus, the methods for treating spent catalysts and adsorbents for eliminating at least in part said contaminants relate to very variable contaminant contents, and consequently, the catalysts or adsorbents can also be found, at the end of the treatment (for example, the regeneration), with variable contaminants and contents. It was therefore necessary to improve the quality of the catalysts or adsorbents obtained. A method for separation of catalysts or adsorbents according to the nature and the content of contaminants was therefore sought.

It was possible to sort out catalysts or adsorbents at the end of the possible treatments to eliminate the contaminants. The applicant did not choose this path. By sorting out catalysts depending on the presence/content of contaminants upstream from the treatment method, the quantities of catalyst to be treated are limited.

Furthermore, the invention is particularly advantageous in that the treatment method can then be adapted to the content of contaminants from the batch of catalyst or adsorbent to be treated. In other words, the method is designed to sort the catalysts or adsorbents based on the content of contaminants and to separate the catalysts and adsorbents according to predetermined contents, in particular based on the treatment methods being considered or based on constraints of reusing catalysts in the industrial methods.

Consequently, the catalysts or adsorbents that are lightly loaded with contaminants are reused in an industrial method (for example, a new cycle) after optionally one or more treatments (for example, regeneration). The catalysts or adsorbents that are too heavily loaded are directed to final recycling to recover the upgradable components.

In the case of reuse, these solids can be subjected, according to their content of contaminants, to suitable treatments for the purpose of their reuse in an industrial plant (regeneration, rejuvenation, lixiviation of metals, etc.). According to a common definition (Dictionary of Scientific and Technical Terms, McGraw-Hill), lixiviation is the dissolution by a liquid solvent of a soluble material (here, a metal) that is contained in a mixture with an insoluble solid.

Likewise, when these solids are sent to the final recycling, the suitable treatments can be selected based on their contaminant content: for example, a treatment of the pyrometallurgical or hydrometallurgical type.

"Regeneration" is defined as the methods whose purpose is to eliminate the coke that is deposited on the spent catalysts or adsorbents in such a way that the catalyst becomes active again or the adsorbent becomes selective again. These methods are well known to one skilled in the art. These are generally methods of controlled combustion.

"Rejuvenation" is defined as the methods whose purpose is to restore an activity and that are applied to generally regenerated catalysts. There again, such methods are known to one skilled in the art. These are generally methods with introduction of particular organic molecule(s) on the catalyst.

"Treatment of the pyrometallurgical or hydrometallurgical type" is defined as the methods whose purpose is to separate the various metals for the purpose of upgrading. These methods are well known to one skilled in the art.

A method for separating these catalysts and adsorbents depending on the presence or absence of contaminant(s) and very advantageously based on the contaminant(s) content was therefore sought.

The invention relates to a method for separation of at least one catalyst and/or adsorbent from a homogeneous mixture of catalysts or adsorbents, with said catalysts or adsorbents containing one or more metal, semi-metal or non-metal contaminant(s) deposited on said catalyst or adsorbent grains, method in which the catalyst or adsorbent grains are separated according to a sorting threshold corresponding to a contaminant content and defined by the user, method in which The catalyst grains of said mixture run past an LIBS detection system that detects the wavelength that characterizes said contaminant, The analyzing device associated with LIBS processes the signal that is sent by the detection system by comparing it to a set-point value that indicates the sorting threshold, The analyzing device sends a signal for ordering the evacuation of grains according to its contaminant content, and at least 2 batches—at least one batch of catalysts or adsorbents that are heavily loaded with said contaminant in relation to the sorting threshold and at least one batch of catalysts or adsorbents that are lightly loaded with said contaminant in relation to the sorting threshold—are obtained.

The detection system therefore detects the presence or absence of the contaminant and also its content.

The method is particularly suitable for catalysts or adsorbents to be separated containing at least one of the contaminants Fe, Hg, Ni, V, C, Cl, Na, S, N, Si, P, As.

For example, it is possible after sorting to send a batch that is heavily contaminated with vanadium to final recycling in such a way as to recover at least in part the upgradable materials. The batch that is lightly contaminated with vanadium can be sent to a regeneration method for the purpose of eliminating coke and reusing it in a refining method.

Thus, the lightly loaded catalysts or adsorbents can be separated from the more heavily loaded catalysts or adsorbents, with the separation threshold (sorting) being set by the operator.

In the case of the separation of catalysts or adsorbents that are contaminated by sodium, it is particularly advantageous to separate the catalysts or adsorbents that contain less than 0.3% by weight of Na (separation threshold); they are advantageously reused after an optional treatment such as regeneration, rejuvenation, or lixiviation.

In the case of the separation of catalysts that are contaminated by vanadium, it is particularly advantageous to separate the catalysts that contain little V, for example less than 2% by weight (separation threshold) of V; they are advantageously reused (for example, in the refining methods) after an optional treatment such as regeneration, rejuvenation, or lixiviation, and preferably regeneration.

In the case of the separation of catalysts that are contaminated by vanadium, it may also be advantageous to separate the catalysts that contain a lot of V, for example 12% by weight (separation threshold) or more of V, the former being treated in final recycling to recover the upgradable elements at least in part.

In the case of the separation of catalysts or adsorbents that are contaminated by sulfur, it is particularly advantageous to separate the catalysts that contain, for example, less than 2% by weight (separation threshold) of S; they are advantageously reused after an optional heat treatment under a controlled atmosphere, containing, for example, oxygen to eliminate carbon, and then, for example, hydrogen to restore a reduced metal phase.

This case arises in particular in the guard beds of a unit for catalytic reforming of naphtha or for isomerization of light gasoline, also commonly called "sulfur traps" (because these catalysts or adsorbents are contaminated by sulfur).

In the case of the separation of adsorbents that are contaminated with arsenic, it is particularly advantageous to separate the catalysts that contain, for example, less than 1% by weight (separation threshold) of As; they are advantageously reused after an optional treatment such as regeneration, rejuvenation, or lixiviation.

With the contaminants that result from the use of the catalysts or adsorbents in contact with the hydrocarbon feedstocks, the method relates to the treatment of spent catalysts and adsorbents.

The method can also be applied to the regenerated catalysts or adsorbents. Actually, the thermal regeneration methods are effective for some contaminants such as carbon and sulfur but are generally ineffective for certain contaminants such as vanadium, iron or nickel.

The invention is particularly suitable in the context of the sorting of catalysts for hydrotreatment, hydrocracking or hydroconversion after use, once unloaded from the installations, in an extruded form of the cylindrical, trilobe or multilobe type. The invention is also applicable to any type of balls or extrudates that are used as catalysts or adsorbents in methods that deal with the hydrocarbon feedstocks that are obtained from fossil resources (petroleum, gas, carbon) or renewable resources (biomass).

According to the invention, the dwell time of a grain in front of the LIBS detection system is less than 50 ms, and preferably less than 10 ms.

The method according to the invention makes it possible to detect and to sort a number of grains that is greater than 20 grains per second, preferably 20-100 grains/s or 50-100 grains/s, and even greater than 100 grains/s and that can range up to 1,000 grains per second or more.

In a preferred way, the grains flow in such a way that their spacing is between zero and their characteristic largest dimension, and the measurement frequency is between 1/t and ½t, with t being the dwell time of the grain in front of the LIBS detection system.

Advantageously, the spacing between the grains is at maximum equal to their characteristic largest dimension. This makes it possible to maximize the quantity of material that is treated for a given flow rate of the grains.

Advantageously, the detection system is positioned in such a way that the depth of the field of analysis above the surface of the transport means is between ⅓ and 3 times the characteristic smallest dimension of the grain.

The object of the invention is to propose, for catalysts, which are objects of homogeneous and well-defined shape (cylindrical extrudates, trilobes or multilobes, balls), a sorting method using the very fast LIBS on-line detection means.

The Catalysts or Adsorbents

The catalysts/adsorbents are objects that are well defined in shape, size and composition. Their mixture can be separated according to the invention when this mixture is homogeneous, and quite obviously when there is a difference in the level of contaminant(s) (presence or absence, content) and when this difference can be detected by LIBS.

Furthermore, certain contaminants such as Ni can be found, for example, in catalysts that contain Ni. Differentiation is done by the content: with the Ni of the catalyst having higher contents than the Ni contaminant, the sorting threshold is selected in such a way as to ensure the separation.

The length of the extrudates has a certain distribution around a mean value, this being due to a certain variability of length during the production of catalysts or adsorbents, but also to phenomena of attrition and breakage of extrudates that undergo a certain reduction in length as a result. Hereinafter, the mean length of the extrudates will be referred to as the characteristic largest dimension.

The diameter of a ball or a cylindrical extrudate, or else the circumscribed diameter that is tangent to the peaks of the lobes for a trilobe or a multilobe, is defined as the characteristic smallest dimension of a particle. In a general manner, the term diameter will be used in the entire text as being the characteristic smallest dimension regardless of the particle type.

The diameter of the particles (or grains) is in general well defined, and its dispersion is in general small compared to its mean value.

The Homogeneous Mixture

According to the invention, the catalysts or adsorbents to be sorted come in the form of a homogeneous mixture.

"Homogeneous mixture" is defined as a mixture in which the catalysts or adsorbents have a homogeneous size and/or a homogeneous shape.

"Homogeneous size" means that the characteristic smallest dimensions (also called diameters) are very close.

In general, the catalyst has a shape of balls, or cylindrical extrudates, trilobes or quadrilobes or multilobes with a diameter that is often between 0.5 and 3 mm (often close to 0.9-1.5 mm) and with a length that is equal to 2 to 5 times the diameter of the extrudates. It can be shaped in the form of balls of 0.5 to 10 mm, preferably between 0.5 and 5 mm in diameter, or pellets. The catalysts can also be used in the form of dispersed powders, whose diameter is in general less than 200 microns, but this shaping does not relate to the object of the invention.

It should be noted that these shapes sometimes have defects associated with the production method. For example, extrudates are sometimes slightly curved over the length. These defects are acceptable in the implementation of the method according to the invention.

This homogeneous mixture could be obtained at the end of a preliminary separation step (pre-sorting) based on the physical properties. This sorting can be performed on catalysts having grains of similar diameter, but for which it would be desired to eliminate the particles that are too short, which are not reusable, and which it is suitable to eliminate before the compositional sorting. This pre-sorting can be performed by, for example, sieving or another technique that is known to one skilled in the art for separating solids by their size, or any other sorting method (sorting by density . . . ).

This pre-sorting is advantageous, for example, for separating the elements that are loaded at the top of the reactor, so-called elements of the guard layer, or of the guard bed. These elements are often mixed during an unloading with the catalysts that are located in the lower layers. These elements can be balls, rings, extrudates, pellets, which may or may not contain catalytic elements. They should be separated before the upgradable catalysts are subjected to the compositional sorting system with LIBS detection.

This pre-sorting is also advantageous in the case of catalysts of different shapes (for example, cylindrical or multilobed) having different diameters, for example a mixture of 1.5 mm and 3 mm. The conventional mechanical separation techniques, sieving, for example, can be implemented for recovering each product.

It can also happen that two catalysts of the same shape and dimension but of different composition are loaded into the same reactor. In this case, the invention makes it possible to solve the problem posed by the selective recovery of one or more of the components of the mixture.

The Components of the Catalyst

The substrate of the catalysts and adsorbents is generally based on alumina or silica-alumina or titanium oxide, with the optional presence of zeolite, in particular for the catalysts for hydrocracking, for hydroconversion of distillates, or for hydrotreatment. More rarely, the substrate can consist of activated carbons.

The catalysts contain constituent elements (metals) that impart to the catalyst the catalytic properties that are required for treating certain gaseous streams or petroleum fractions. These metals are, for example, Ni, Mo, Co, W, in particular for the catalysts for hydrotreatment and hydroconversion, such as Pd and Pt, in particular in methods for hydrogenation, dehydrogenation, isomerization, reforming, hydroconversion.

These noble metals are very sensitive to contaminants, in particular sulfur, and are generally placed downstream from the hydrotreatment step. Adsorbents can also contain constituent metals on the substrate; this is the case, for example, of sulfur traps.

Adsorbents may also not contain constituent metals on the substrate; this is the case, for example, with activated carbons that are used in mercury removal.

The active phase of the catalysts for hydrotreatment and hydrocracking contains sulfides of cobalt, nickel, molybdenum or tungsten, which are supported, generally on alumina. The new catalyst is initially prepared with oxides of these metals, which are then sulfurized. In general, the CoMo, NiMo, NiCoMo or NiW combinations are found depending on the reaction objectives. The initial composition of nickel oxide or cobalt oxide is in general between 2 and 10% by weight, preferably at least 3.5%, on the catalyst, and the composition of molybdenum and tungsten is close to 15 to 30% by weight.

The Contaminants

The catalysts or adsorbents in question are the catalysts or adsorbents that are used in the industry, in particular the chemical industry, the industries for production and refining of hydrocarbons (gas, petroleum), the methods for treatment of biomass and/or carbon. The method and the device that are objects of this invention are therefore particularly suitable for treating catalysts for hydrotreatment, hydrocracking, hydroconversion of distillates or petroleum residues, but also methods for pretreatment or for purification of hydrocarbon fractions (guard bed for desulfurization upstream from catalytic reforming, removing mercury . . . ), with the list not being exhaustive.

In a general manner, the methods in question are characterized by the fact that they deal with a hydrocarbon feedstock that contains one or more contaminants that can be deposited on the adsorbent or the catalyst used in the method.

The deposition of this contaminant can be the result of a desired reaction, for example a deposition of vanadium during the hydrotreatment of residues, or else may result from an undesirable secondary reaction, for example the deposition of carbon or coke or arsenic.

The contaminants that are deposited during the operation are most often carbon, sulfur and nitrogen, chlorine, silicon, phosphorus or sodium for the non-metal contaminants, Ni, V, Fe, Hg for the metal contaminants, or As for the semi-metal contaminants, depending on the treated fractions and on the origin of the refined crudes. These are the most known contaminants, with this invention being applicable to any type of contaminant.

The quantity of contaminants in the catalysts is not limiting for the implementation of the invention, provided that it is detectable by the LIBS technique.

The problem of the separation is particularly crucial for vanadium.

The vanadium content of the catalysts is based on the position of each grain in the reactor, the service life, the vanadium content of the treated feedstock and operating conditions. The V contained in the distillate fractions or residues that are treated in these methods is present at contents that vary based on the nature of the crudes and the petroleum fraction being considered. Thus, in a method for pretreatment of a catalytic cracking feedstock (CCF), the content of V of the feedstock can be, for example, close to 1 to 10 ppm, while it can reach 100-300 ppm and even more in certain residues. As a result, the V content of the spent catalysts can range—depending on the methods—from a fraction of one percent to approximately 100% by weight of new catalyst.

The Detection by LIBS Technique

LIBS makes it possible to properly focus on and position the detection to make it more effective.

This is an elementary (or compositional) analysis technique, increasingly used for the direct analysis of solids and liquids. The increasing interest in this technique stems from its numerous advantages including, in this case, a possible in-situ analysis without a particular preparation of samples, a fast in-situ analysis, simplicity of use, and specific focusing.

The principle relies on the focusing of a laser pulse on the surface of the sample. This focusing of laser pulses of several nanoseconds, and even femtoseconds, and an energy on the order of several tens of millijoules to the point to be analyzed on the material causes the formation of a microplasma. This microplasma feeds on the composition of the surface of the sample, which generates the vaporization and the ionization of the material, and then cools over time.

The size of the analysis point is usually on the order of several microns, and even ten microns. The atoms and the ions of the material present in the microplasma emit by deenergizing photons whose wavelength is characteristic of the chemical element. A spectrometer in the UV/visible range collects, optionally using an optical fiber, and reflects the light emitted by the plasma. The emission lines, generated by the analyzed sample, make it possible to identify the elements that are present in the sample (qualitative analysis) and therefore to know the chemical radicals that composed the sample. Their intensity can also be measured and compared to the one measured for a range of samples of known concentration, so as to measure the elementary composition of the sample (quantitative analysis).

In the case of this invention, a quantitative analysis makes it possible to measure the contaminant content in the catalyst or adsorbent that is to be separated, for example the sodium content in a hydrotreatment catalyst.

The response speed of the LIBS is a decisive advantage for the productivity of the sorting with objects of small size such as the catalysts.

The grains of catalyst or adsorbent are subjected to a laser radiation. In return, in an analyzing device, the associated emission is analyzed by spectroscopy with a wavelength that is selected to make possible the detection of the contaminant on the catalyst or adsorbent by measuring the intensity of the peak(s) relative to this contaminant.

To do this, the analyzing device associated with LIBS processes the signal sent by the detection system by comparing it to a set-point value that indicates the presence of the contaminant, and also that indicates the sorting threshold.

The sorting threshold can correspond to 0% by weight, and therefore the presence or absence of the desired constituent element is detected, and the sorting is carried out in this presence or absence; 0% corresponds to the detection limit of the LIBS for the element being considered.

The sorting threshold can correspond to a content that is different from 0%, selected by the user according to the desired element and the constraints/objectives of the user. The threshold of the element is selected in such a way as to make possible the separation of the element from the mixture.

The wavelengths that are associated with the contaminant are known to one skilled in the art, as well as the possible interferences with other elements.

For example, for sodium, numerous atomic emission lines located between $\lambda=588$ and 590 nm or between $\lambda=818$ and 820 nm. Preferably, the lines with a wavelength of 588.995 or 589.592 nm are used for their high intensity and their absence of interference with the constituent elements of the hydrotreatment catalyst Co, Ni, Mo, W, Al and Si. Alternatively, the lines with a wavelength of 818.326 or 819.482 nm are used by themselves or in combination with any other line of the spectrum, constituting the sample. The Na is particularly emissive and measurements of content in the catalyst grains are conceivable up to contents as low as 0.05%, which makes it possible to sort the catalysts depending on a sorting threshold value that is selected by the user in the interval between 0.1 and 1% by weight of Na.

In the case of the contaminant sulfur deposited on a catalyst (which contains, for example, nickel on the guard bed of the reformer), the sorting threshold value selected by the user in the interval is in general between 1 and 3% by weight of S. The wavelength is between $\lambda=920$ and 925 nm or between $\lambda=180$ and 183 nm, for example. Preferably, the lines with a wavelength at 921.287 or 922.809 nm are used for their high intensity; they are also used for their absence of interference with the elements that constitute the reforming catalyst. Alternatively, the lines with a wavelength at 180.731, 182.034 or 182.625 nm are used by themselves or in combination with any other spectrum line that constitutes the sample.

In the case of the contaminant vanadium deposited on a catalyst for hydrotreatment or hydroconversion of the residue, the sorting threshold value selected by the user in the interval can be between 1 and 2% by weight of V to sort the catalysts that are reusable. The wavelength is between $\lambda=600$ and 620 nm or between $\lambda=384$ and 390 nm or else at 309-311, for example. Preferably, a combination of 5 lines between 600 and 620 in combination with any other line of the spectrum that constitutes the sample is used for the effectiveness of detection of vanadium within a hydrotreatment or hydroconversion catalyst. It is also conceivable to select a sorting threshold value at around 12% of V so as to sort the catalysts that will then be directed to the recycling and the recovery of the vanadium.

In the case of the contaminant arsenic that is deposited on a hydrotreatment catalyst, the sorting threshold value selected by the user is, for example, 1% by weight of As; the wavelength is between $\lambda=189.042$ nm or 278.022 nm or else between $\lambda=244$ and 246 nm. Preferably, the lines with a wavelength at 278.022 nm or 189.042 nm are used by themselves or in combination with any other line of the spectrum that constitutes the sample.

It is necessary to emphasize that the thresholds indicated above are given by way of indication and that it is, of course, possible to have higher values depending on sorting constraints desired by the operator.

So as to improve the detection sensitivity, it is possible to make an analysis with several wavelengths, by using, for example, multiple spectrometers coupled to the same light beam and operating in parallel.

The detection system is preferably adjusted in such a way that the depth of field of the analysis above the surface of the transport means is between ⅓ and 3 times the characteristic smallest dimension of the catalyst grain (the diameter of the extrudate in the case of an essentially cylindrical particle, the diameter of the grain in the case of a spherical particle) to make possible an ultra-fast detection of the composition of the grains.

In practice, the analyzing device makes it possible to restore the composition in the desired element with a response time t that is less than 50 ms, preferably less than 10 ms.

The dwell time of a grain in front of the detection system is less than 50 ms, and preferably less than 10 ms, and can range up to less than 1 ms. The number of grains detected is greater than 100 grains/s for a detection time of less than 10 ms and can reach 1,000 grains/s for an analysis time of less than 10 ms.

In a preferred form of the invention, the catalyst grains are spaced, preferably uniformly, by a distance preferably corresponding to the characteristic largest dimension of the catalyst grains, or the mean length of the catalyst grains.

The measurement/detection is repeated at intervals.

When the grains are spaced by their mean length, the measurement frequency is equal to ½t, with t being the dwell time of the grain in front of the detection system. When the grains flow in a contiguous way (the grains are contiguous; their spacing is equal to zero), the frequency is equal to 1/t.

In a more general way, the grains, preferably cylindrical extrudates or multilobes, flow in such a way that their spacing is between zero and their length, and the measurement frequency is between 1/t and ½t, with t being the dwell time of the grain in front of the LIBS detection system.

The spacing between the grains is monitored by the means that are adjusted depending on the detection time of the LIBS detection system.

For example, these are the means for monitoring the supply (flow rate) of the catalyst grains to the transport means (rolling belt, vibrating conveyor, etc.) and the speed of said means.

In a general way, the conditions of the method are adjusted in such a way that a number of grains are treated, which number is greater than 20 grains per second and can range up to 1,000 grains per second and per LIBS detector, and that the response time of the LIBS detection system is less than 50 ms, preferably less than 10 ms.

In an optional manner, the presence of grains can be detected using another optical device, for example a camera, in such a way that the triggering of the laser of the LIBS system is synchronized with the passage of the grain under the laser beam.

In a preferred embodiment of the invention, each catalyst grain is exposed to the detection system.

In a preferred embodiment of the invention, it is then possible to treat at least 20 grains per second with the same measuring device, for example 20-100 grains/s, preferably more than 100 grains per second, and up to 1,000 grains per second or more.

It is also possible to have multiple detection systems in parallel for operating at high speeds. Thus, the use of 5 detection systems operating in parallel with 200 grains/s will make it possible to reach a flow rate of 1,000 grains/s.

The Determination of the Contaminant Content

The LIBS system measures the intensity of the peak(s) relative to the contaminant. The user selects a sorting threshold value included in the values indicated above, or greater, according to the sorting requirements thereof.

The spectrometric analysis with the wavelength(s) being considered make(s) it possible to work back to the concentration by mass of the contaminant on the adsorbent or the catalyst owing to a preliminary calibration.

Depending on the calibration that the operator performs, the set-point value (corresponding to the presence of the contaminant or the sorting threshold) is entered into the LIBS system. This is perhaps a content or any other value connected in a significant manner to the content (this can be the intensity of the peak . . . ); all of these techniques are well known to one skilled in the art.

After comparison between the set-point value and the measured value, the system acts to evacuate the grain to the corresponding storage.

It is necessary to emphasize that the presence of a specific contaminant can be correlated with the content of another contaminant. This constitutes an advantage if one of the two contaminants is more easily detectable with LIBS, because of one or more lines being more emissive, or else because of the interference of another element that disrupts the signal of one contaminant but not the other. This can also be a deliberate choice linked to the use of a spectrophotometer whose spectral band comprises the lines of one contaminant and not the other. Thus, the V contaminant content in the catalyst can be approximately correlated with the Ni contaminant content in the case of a catalytic method processing a feedstock that contains Ni and V. The detection of the V concentration in the catalyst therefore makes it possible by correlation to access the Ni content and also to perform a sorting depending on the Ni content.

Likewise, in certain cases, a contamination with V can be associated with a contamination with Na. This can also be a deliberate choice to sort on the basis of the Na element, whose signal is possibly more sensitive than that of V.

The Separation of Grains

When the LIBS detection system detects the contaminant in one or more grains and preferably also determines the state of the grain in relation to the sorting threshold, it sends a signal to the means for evacuating this grain to be separated in such a way as to separate said grain from said mixture.

The detection system is connected to a system for controlling the evacuation means of the grains containing the desired characteristic contaminant (such as sodium, for example). These means are located in the area of the transport means (conveyor belt . . . ), and most often they are located at the end downstream from (leaving) the transport means.

These means are actuated with a temporal offset depending on their distance with the detection system. An example of an evacuation means that makes it possible to direct the grains in different directions is the use of compressed air. The compressed air jet or the absence of a compressed air jet makes it possible to direct the grain toward the different sorting classes, for example the grains that contain more than X % of a contaminant are evacuated upward whereas the grains that contain less than X % of the contaminant are evacuated downward.

For example, if the grain of catalyst or adsorbent contains the desired contaminant with a content that is greater than the sorting threshold set by the operator (0.25%, for example, for sodium), then the means are actuated and make possible a deviation of the flow of the grain toward a receptacle A. If, in contrast, the catalyst or the adsorbent contains the contaminant with a content that is less than the sorting threshold set by the operator (0.25%, for example, for the Na), then the means are not actuated and the catalyst flows normally to another receptacle B.

In the case where it is desired to sort the catalysts or adsorbents based on multiple contents of different contaminants, multiple LIBS detection systems are advantageously used, each having a wavelength adapted to the characteristic element to be separated. The evacuation means are adapted in terms of function.

The many sorting options will not be presented in detail here; there may be more than one sorting in the presence of several LIBS detectors. One skilled in the art will adapt the method according to the invention depending on his needs.

The invention also relates to a device for separating at least one catalyst and/or adsorbent from a homogeneous mixture of catalysts and/or adsorbents, with said catalysts or adsorbents containing one or more metal, semi-metal or non-metal contaminant(s) deposited on said grains of catalysts or adsorbents, with the device for separation and sorting making it possible to separate the catalysts or adsorbents according to a sorting threshold corresponding to a contaminant content and defined by the user, with said device comprising:

A chain for transporting the mixture of catalysts equipped with a transport means, means for monitoring the flow rate of grains on said means, and means for monitoring its speed, with said means being adjusted in such a way that the dwell time of a grain in front of the LIBS detection means is less than 50 ms, and preferably less than 10 ms, and the number of sorted grains is at least 20 grains/s, preferably at least 100 grains/s, and in an even more preferred way at least 200 grains/s, An LIBS detection system comprising at least one laser past which the grains run, with the detection time being less than 50 ms, and preferably less than 10 ms, and the wavelength being that of the desired contaminant, said system detecting the grain that is loaded with said contaminant and measuring the intensity of the peak associated with said wavelength, At least one analyzing device (8) and at least one control means (10), with said analyzing device processing the signal sent by the detector by comparing it to a set-point value that indicates the sorting threshold, At least one means for evacuation of the grains to be separated, with said means being actuated from said control means according to the content of said desired contaminant.

Conventional means for conveying (vibrating tube, vibrating elevator, etc.) and for storing grains to be sorted and then sorted grains can be used at different locations of the sorting method.

Advantageously, the transport means is a rolling belt (or conveyor belt). This can also be a die equipped with an endless screw that has a hollowed-out shaft and is equipped with at least one opening suitable for detection and at least one opening suitable for separation of catalyst grains. This transport means can also be a vibrating belt or tube.

Preferably, the transport means is a conveyor belt that is preferably crenellated, with the gaps being between 0.5 and 3 deep, preferably 0.7 and 1.3 times the characteristic smallest dimension of the grains, corresponding to the diameter in the case of a sphere or an extrudate.

In a preferred way, the adjustment of said means of the transport chain is carried out in such a way that the grains flow with a spacing of between zero and their characteristic largest dimension; the measurement frequency is between 1/t and ½t, with t being the dwell time of the grain in front of the LIBS detection system.

The grains are preferably cylindrical extrudates, trilobes, or multilobes.

When the grains are spaced by their mean length, the measurement frequency is equal to ½t, with t being the dwell time of the grain in front of the detection system. When the grains flow in a contiguous way (the grains are contiguous; their spacing is equal to zero), the frequency is equal to 1/t.

The device of the invention is particularly well suited to implement the method of the invention. Also, the characteristics described above for the method apply to the device.

Advantageously, the detection system is positioned in such a way that the depth of the analysis field above the surface of the transport means is between ⅓ and 3 times the characteristic smallest dimension of the grain.

Advantageously, the dwell time of a grain in front of the LIBS detection system is less than 50 ms, and preferably less than 10 ms, with the analyses being repeated at intervals at most equal to the dwell time of the grain of the characteristic smallest dimension.

DETAILED DESCRIPTION OF THE METHOD AND SEPARATION DEVICE

The catalyst or adsorbent grains initially stored in barrels, containers, silos or in bags are then generally transferred into a buffer tank, for example a hopper, with this tank feeding a transport chain that advantageously comprises an unrolling belt such as a conveyor belt or a vibrating tube or channel, and which comprises means for monitoring the flow rate of grains on the rolling belt.

The grains that are transported run past the LIBS quantitative and qualitative analysis system of the contaminant content making possible the presence of contaminant and preferably making it possible to determine whether the grains have a smaller or larger content of contaminant in relation to one or more sorting thresholds defined by the operator. There may be one or more thresholds for each contaminant according to the needs of the operator.

BRIEF DESCRIPTION OF THE DRAWINGS

By way of illustration, FIG. 1 depicts an embodiment that is preferred but non-limiting of the method and the device that are the object of this invention.

The unsorted mixture of catalyst or adsorbent grains (1) is brought on a means (2) that makes it possible to monitor the flow rate of grains on the rolling belt (5). The intake means of the mixture (3) can be manual (unloading of a bag, for example) or automatic (by controlled unloading of a silo, for example).

The invention is described with a rolling belt as a transport means, but the description is entirely transposable with another transport means, such as, for example, the vibrating channel described above.

The means that make it possible to monitor the flow rate are means that are well known to one skilled in the art, such as, for example, inclined vibrating plates, making possible the uniform spreading of the catalyst grain and the adjustment of the flow rate of the catalyst on the plate toward the rolling belt. One skilled in the art can thus adjust the distance between two grains on the transport chain and consequently adjust the detection frequencies or else, conversely, it is possible to adjust the distance depending on the detection frequencies.

Figure 1:
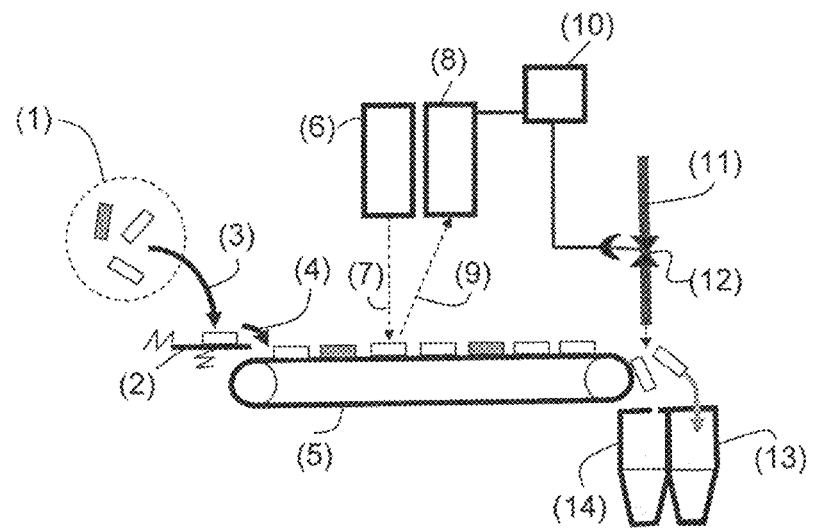
FIG. 1 depicts a preferred embodiment by way of illustration.

By way of example, in FIG. 1, we showed at (2) a vibrating plate in two orthogonal directions. With this type of equipment, it is possible to adjust the vibration frequencies for modulating the flow rate of solid (4) toward the rolling belt (5), to adjust the distribution between the grains over the passage section, and thus to monitor the spacing between the grains based on the travel speed of the belt.

Preferably, in an optimal manner, the device will be adjusted so that the distance between the grains is at maximum equal to the mean length of the grains.

Figure 2:
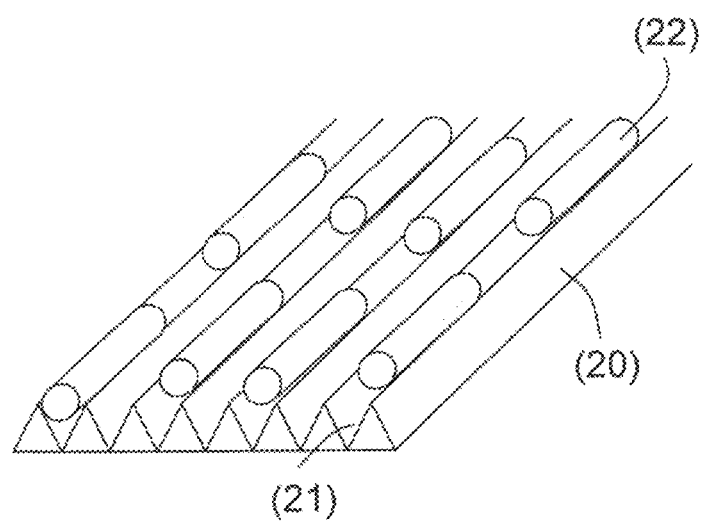
FIG. 2 depicts a crenellated belt.
Figure 3:
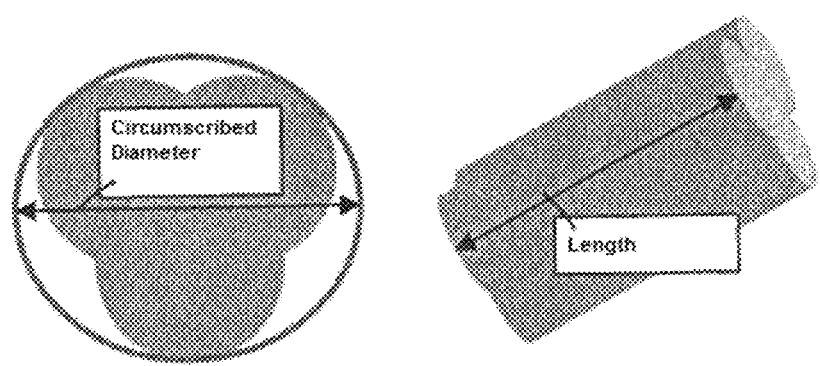
FIG. 3 shows grain shapes.

Leaving the flow rate monitoring means (2), the catalyst grains fall on the rolling belt, which can be a simple flat conveyor belt, or a crenellated belt, as shown in FIG. 2.

The crenellated belt of FIG. 2 has a manifest advantage—when in particular extrudates are sorted—in that it makes it possible, in an advantageous manner, to orient the grains in the direction of flow. The flow of the grains is thus more uniform and spaced, which promotes the detection and the separation, and improves the productivity of the installation. In a general way, regardless of the grain shape, the crenellated belt keeps the grain from moving under the action of the vibrations of the belt and/or pulses of the laser.

In the case of a crenellated belt (20), a form of gap (21) that has the shape of an equilateral triangle as shown in FIG. 2 is advantageous; the depth of the gaps on the belt is then ideally between 0.7 times and 1.3 times the characteristic largest dimension of the grains, the diameter of the catalyst grains in the case of balls, the mean length in the case of cylindrical extrudates or trilobes or multilobes.

The grains (22) are positioned on the belt (20). The travel speed of the belt is adjusted so as to optimize the production capacity, on the one hand, and the capacity of the system to detect the desired contaminant in the catalyst grains.

An attempt will preferably be made to ensure that the dwell time of a grain is less than 50 ms, and is preferably less than 10 ms. More generally, the dwell time is the smallest possible, consistent with the response time of the detection system.

Under these conditions, for example, for a cylindrical extrudate with a length that is equal to 5 mm, the speed is preferably between 0.1 and 5 m/s.

The detection system comprises at least one laser (6), at least one spectrometer (or analyzing device) (8) and at least one means (10) for controlling the opening or not of at least one evacuation means.

A laser (6) emits radiation focused on the surface of the sample (7). Following the pulse on the order of the femtosecond to the nanosecond between the laser and the sample, a plasma fed by the composition of the sample is generated and in several milliseconds sends wavelengths suitable to the composition of the sample (9).

The emissions of the sample (9) are analyzed by a spectrometer (8) with specific wavelengths of the contaminant having to be detected. In an optional way, at least one optical fiber is used between the plasma and the spectrophotometer. It is possible to work with several wavelengths simultaneously by positioning on the light beam several spectrometers in parallel that work simultaneously with different wavelengths.

For example, to measure the sodium content in the hydrocracking or hydrotreatment catalysts, the wavelength at 588.995 or 589.592 nm will be used owing to its high intensity. The lines at 818.326 nm or 819.482 nm can also be used. These four lines make it possible to detect the presence of sodium by minimizing the interference with Ni, Co, Mo, Al, W or Si.

Depending on the requirements, it is possible to analyze all of the grains running past the detection system (6-7-8-9) on the rolling belt (5), overall or individually, by using several laser systems (6) in parallel in such a way as to cover the width of the belt and by adapting or decoupling also the laser and the spectrometer (8) analyzing the emissions (9).

It is also possible to choose to operate statistically, by analyzing only a fraction of the flow, or to consider a movement over the width of the lasers (6) and the spectrometer(s) (8).

The analyzing device (the spectrometer) (8) is connected to control means (10) that make it possible to convert the results of the analysis in action to act on said evacuation means (here, the valve 12).

These means consist of, for example, a computer that makes it possible to initiate the opening of a valve (12).

Thus, for example, when the analyzing device (8) detects that the grain has a larger content than the set-point value (for example, the contaminant sorting threshold), it sends a signal to the control means (10) that actuates the opening of the valve (12).

The former is located on a duct of inert fluid (air, for example) under a pressure that is if possible greater than 5 bar (preferably air) to promote the creation of a jet of gas (air) that is sufficient to evacuate the grain.

The valve (12) opens during a determined period DT1 and then closes again automatically. The opening of the valve makes it possible to generate a jet at the lower end of the duct (11). It acts with the duct as a gas (air) ejection nozzle. Advantageously, the duct (11) is positioned at the end of the conveyor belt at a distance of at most 10 cm from the end of the belt (based on the travel speed of the belt, the lower the unrolling speed of the belt, the closer the duct (11) approaches the end of the belt), at a level above the belt (5) preferably encompassed between 2 and 10 times the characteristic largest dimension of the catalyst grain (its length in the case of an extrudate).

It is possible to position one or more ducts (11) in parallel depending on the width of the conveyor belt and the shape of the end of the duct.

In the case of a spherical duct end fitting, the diameter of the end fitting of the duct is preferably less than or equal to the mean length of the grains.

If the belt makes possible the simultaneous transition in the width of N particles simultaneously, it is possible to position up to N tubes (11) in parallel, each having their valve, the valves being controlled simultaneously or separately by the control means (10) depending on the number of analyzing devices used in parallel.

It is also possible to work with a single duct (11) but whose rectangular section end could create a pencil gas jet, with the thickness of the jet then preferably being less than or equal to the mean length of the grains.

So as to take into account the distance between the detection means and the evacuation means, the control system initiates the opening-closing cycles with a delay that is based on the distance to travel between these two points. For example, if the belt length between the focal position of the analyzing device on the belt (9) and the evacuation means (valve, air injection nozzle (12)) is 3 m and the travel speed on the belt is 3 m/s, a delay of one second is to be taken into account, optionally to correct, depending on the response time of the analyzing device (8), the control means (10) or the valve (12).

For the requirements of the invention and to be selective, the opening-closing cycle of the valve is to be fast and cohesive with the dwell time of the grains in front of the detector. Preferably, the opening-closing cycle time will not exceed 1 and 5 times the dwell time of the grain in front of the detection means, preferably less than 3 times this mean dwell time.

Thus, technologies of valves and actuators will be selected so as to have an opening-closing cycle of between 5 and 250 ms depending on the travel speed of the transport means (5).

The gas jet (for example, air) created during this period has a speed that is at least equal to 5 times the terminal drop speed of the grain, preferably 10 times the terminal drop speed (in the case of a hydrotreatment extrudate, the terminal drop speed is in general close to 5 m/s and between 2 and 7 m/s).

When the actuator initiates the opening of the valve, the gas jet diverts the path of the grain to a receptacle (14) that harvests all of the grains in which the contaminant content is greater than the sorting threshold defined by the operator.

If the actuator is not triggered, then the path of the grain exiting from the conveyor belt describes a normal parabola depending on the unrolling speed of the belt and the terminal drop speed of the particles. The grain then falls into a receptacle (13) that harvests all of the grains to be eliminated that do not contain the undesirable element.

Thus, the grains collected at (13) will constitute a new batch that has, for example, a contaminant content that is lower than the sorting threshold defined by the operator.

In relation to the prior art, the invention makes possible a rapid sorting depending on the contaminant content of at least 20 to 100 objects (catalyst grains)/second, in general at least 50 and even 100 objects/second, or even beyond 100 objects/s, and its use allows up to 1,000 objects/second or more. The LIBS technique therefore allows itself alone a significant productivity.

Another advantage of the invention is to be able to be implemented in air or any other atmosphere (not interacting with the detection or the grains).

Example 1

Sorting of a Batch of a Mixture of Hydrotreatment Catalysts Containing Ni and Mo and an Na Contaminant:

120 grains of catalysts with a batch of catalysts were analyzed by LIBS from a batch of 3 g that initially was analyzed by X fluorescence (Panalytical PW2404, Rh tube). The mean contents of the elementary analysis by X fluorescence were provided in Table 1.

TABLE 1

| V (% by Weight) | Fe (% by Weight) | Na (% by Weight) | Ni (% by Weight) | Mo (% by Weight) |
| --- | --- | --- | --- | --- |
| 0.16 | 0.31 | 0.31 | 2.90 | 13.9 |

An LIBS laboratory device (MobiLIBS III, IVEA) was used for this test; it consists of a laser (Brio, Quantel, Nd-YAG at 532 nm) and a spectrometer (Mechelle Andor, 200-900 nm). The device was used in single-laser-shot mode, and each catalyst grain was analyzed under the following conditions: 12 mJ/spot of 140 µm/3-5 ns of pulse time.

Starting from the number of hits measured on the spectrometer in the various lines of Na (lines at 588.995, 589.592, 818.326 and 819.482 nm), the 120 catalyst grains were sorted into three families: the catalyst grains having fewer than 60,000 hits, those between 60,000 and 120,000 hits, and those with a number of hits greater than 120,000.

0.57 g of grains having a signal with fewer than 60,000 hits was collected, while 0.53 g of grains having a signal of between 60,000 and 120,000 hits was recovered. 0.03 g of grains having a signal with a number of hits greater than 120,000 was observed.

The batch of grains of 0.57 g and 0.53 g are sufficient to carry out an analysis of Na by atomic absorption spectrometry (Agilent SpectrAA 240 FS) after mineralization (0.2 g of sample+2 ml of HClO4 70%+4 ml of HF 40%) [sic]. The Na content measured in the batch of 0.57 g and having an LIBS signal with less than 60,000 hits was 0.14% Na while the batch of 0.53 g and having an LIBS signal of between 60,000 and 120,000 hits was 0.28% Na. This test confirms that sorting on individual grains is possible using the LIBS technique.

Example 2

Sorting of a Batch of a Mixture of Hydrotreatment Residue Catalysts with a Threshold for Vanadium of 1%.

In the same way as the preceding example, 50 grains of two families of catalysts (cat 1 and cat 2) having different vanadium contents were subjected to LIBS analysis. The characteristics of the catalysts in terms of chemical composition obtained by X fluorescence (Panalytical PW2404, Rh tube) are provided in Table 2:

TABLE 2

|  | V (% by Weight) | Fe (% by Weight) | Na (% by Weight) | Ni (% by Weight) | Co (% by Weight) | Mo (% by Weight) |
|---|---|---|---|---|---|---|
| Cat 1 | 0.45 | 0.14 | 0.15 | 0.79 | 2.22 | 11.0 |
| Cat 3 | 1.73 | 0.24 | 0.35 | 1.13 | 2.17 | 11.3 |

The LIBS system used is equipped with a laser (Quantel, Centurion, 1064 nm, 100 Hz) and two spectrometers with high acquisition frequency (HR2000+, grating at 1800 lines/mm, resolution of 0.11 nm for the 554-663 nm zone/HR2000+, grating at 2400 lines/mm, resolution of 0.09 nm for the 298-395 nm zone). The mean value of the LIBS signal, on the 50 grains of the Cat 1 family containing on average 0.45% of V, is 4,000 hits on the line at 609.022 nm versus 29,000 hits on the line at 309.311 nm. The same experiment conducted on the 50 grains of the Cat 3 family, containing on average 1.7% of V, provides mean values of 10,000 hits on the line at 609.022 nm versus 48,000 hits on the line at 309.311 nm. The signal measured on the line at 609.022 nm is on average 2.5 times higher over the 50 measured grains of the batch containing 1.73% of V in relation to the batch that contains only 0.45% of V. The same calculation performed on the line at 309.311 nm shows a mean signal that is 1.6 times higher for the batch that contains 1.73% of V in relation to the batch that contains only 0.45% of V. In the two cases, the LIBS technique therefore readily makes it possible to differentiate a batch of catalysts containing more or less than 1% of V of contaminant.

Example 3

Sorting of a Batch of a Catalyst Mixture that is Used in a Guard Bed on the Reformer and is Contaminated with S at a Level of 2%:

50 grains of catalysts of a batch of catalysts in a guard bed were analyzed by LIBS to determine their S content and to decide whether these grains should be recycled or eliminated. The LIBS system used for these tests is equipped with a laser (Quantel, Centurion, 1064 nm, 100 Hz) and a spectrometer centered on the region 578 at 1011 nm (HR2000+, grating at 600 lines/mm). The lines of S with a wavelength of 921.287 or 922.809 nm are used for this detection of S, and a weak signal is detected on the analyzed catalyst grains. Starting from the number of hits measured on the line at 921.287 nm, sorting is carried out on the individual grains: the grains having a higher signal of more than 500 hits are ejected whereas the grains having a lower signal of less than 500 hits are retained.

Of the 50 initial grains, 13 grains were ejected. Despite the small quantity of material, a semi-quantitative X-fluorescence analysis (Uniquant, Thermo Perform'X, Rh tube) by depositing the grains in a measurement cell (XRF sample cells, Fluxana SC-3340, 40 mm, 6 µm polypropylene film) was made. The mean and semi-quantitative content measured on the ejected grains is 4.3% S, whereas an analysis carried out on the batch of the retained 37 grains shows a value of 1.2% of S. The sorting carried out on the basis of the detection of S at the wavelength of 921.287 nm is therefore effective for separating the catalyst grains in the guard bed that may or may not be contaminated by S at a level of 2%.

The invention claimed is:
1. A method for separation of at least one catalyst and/or adsorbent from a homogeneous mixture of catalysts and/or adsorbents that are spent catalysts or adsorbents, with said catalysts or adsorbents containing one or more metal, semi-metal or non-metal contaminant(s) that is Fe, Hg, Ni, V, C, Cl, Na, S, N, Si, P, or As, with said contaminant(s) being deposited on said catalyst or adsorbent grains, said method comprising separating the catalyst or adsorbent grains according to a sorting threshold corresponding to a contaminant content and defined by the user,
   running catalyst grains of said mixture past an LIBS detection system that detects a wavelength that characterizes said contaminant,
   sending to an analyzing device associated with LIBS processes a signal from the detection system and analyzing the signal by comparing it to a set-point value that indicates the sorting threshold,
   sending by the analyzing device a signal ordering the evacuation of grains according to contaminant content, and obtaining at least 2 batches—at least one batch of catalysts or adsorbents that are loaded with said contaminant greater than the sorting threshold and at least one batch of catalysts or adsorbents that are loaded with said contaminant less than the sorting threshold,
   treating the catalysts that are loaded with contaminant less than the sorting threshold before being reused in an industrial method optionally by regeneration, rejuvenation, or lixiviation and
   catalysts that are loaded with contaminant greater than the sortie threshold are treated in final recycling to recover upgradable components.
2. The method according to claim 1, in which the sorting threshold is 0%.

3. The method according to claim 1, in which for Na as a contaminant, the sorting threshold is 0.3% by weight, with the grains containing less than 0.3% by weight being separated and being reused after treatment.

4. The method according to claim 1, in which for V as a contaminant, the sorting threshold is 12% by weight, with the catalyst grains containing 12% by weight or more being separated and being treated in final recycling to recover the upgradable elements.

5. The method according to claim 1, in which for V as a contaminant, the sorting threshold is 2% by weight, with the catalyst grains containing less than 2% by weight being separated and reused after an treatment optionally by regeneration, rejuvenation, or lixiviation.

6. The method according to claim 1, in which for S as a contaminant, the sorting threshold is 2% by weight, with the grains containing less than 2% by weight being separated and being reused after treatment optionally by regeneration, rejuvenation, or lixiviation.

7. The method according to claim 1, in which for As as a contaminant, the sorting threshold is 1% by weight, with the grains containing less than 1% by weight being separated and being reused after treatment optionally by regeneration, rejuvenation, or lixiviation.

8. The method according to claim 1, in which the catalysts or adsorbents come in the form of cylindrical extrudates, balls, trilobes, or multilobes.

9. The method according to claim 1, in having a dwell time of a grain in front of the LIBS detection system of less than 10 ms, and a number of detected/analyzed grains of at least 100 per second.

10. A device capable of separating and sorting at least one catalyst and/or adsorbent from a homogeneous mixture of catalysts and/or adsorbents, with said catalysts or adsorbents containing one or more metal, semi-metal or non-metal contaminant(s) deposited on grains of catalysts or adsorbents, with the device separating the catalysts or adsorbents according to a sorting threshold corresponding to a contaminant content defined by the user, with said device comprising:

a chain transporting the mixture of catalysts, a monitor of the flow rate of grains transported, and monitor of speed, with said transport being adjusted in such a way that the dwell time of a grain in front of a LIBS detection means is less than 50 ms, and the number of sorted grains is at least 20 grains/s, an LIBS detection system comprising at least one laser past which the grains run, having a detection time less than 50 ms, and a wavelength that of the desired contaminant, said system detecting the grain that is loaded with said contaminant and measuring the intensity of the peak associated with said wavelength, at least one analyzing device (8) and at least one control (10), with said analyzing device processing the signal sent by the detector by comparing it to a set-point value that indicates the sorting threshold, at least one evacuation port for grains to be separated, with said port being actuated from said control according to the content of said desired contaminant.

11. The device according to claim 10, in which the transport is a crenelated belt, having a depth of gaps between 0.5 and 3 times characteristic largest dimension of the grains.

12. The method according to claim 1, wherein treatment of the catalyst with contaminant less than the sorting threshold is by regeneration, rejuvenation, or lixiviation.

13. The method according to claim 3, wherein treatment of grains containing less than 0.3% by weight is by regeneration, rejuvenation, or lixiviation.

14. The method according to claim 5, wherein treatment of grains containing less than 2% by weight is by regeneration, rejuvenation, or lixiviation.

15. The method according to claim 6, wherein treatment of grains containing less than 2% by weight is by regeneration, rejuvenation, or Lixiviation.

16. The method according to claim 7, wherein treatment of grains containing less than 1% by weight is by regeneration, rejuvenation, or lixiviation.

* * * * *